United States Patent [19]
Andersson et al.

[11] Patent Number: 5,939,409
[45] Date of Patent: *Aug. 17, 1999

[54] PROCESSES FOR THE PRODUCTION OF ANTI-INFLAMMATORY STEROIDS

[75] Inventors: Paul Andersson, Södra Sandby; Bengt Axelsson, Genarp; Ralph Brattsand, Lund; Arne Thalén, Bjärred, all of Sweden

[73] Assignee: Astra Aktiebolag, Sodertalje, Sweden

[ * ] Notice: This patent is subject to a terminal disclaimer.

[21] Appl. No.: 08/944,676

[22] Filed: Oct. 7, 1997

Related U.S. Application Data

[63] Continuation of application No. 08/094,207, filed as application No. PCT/SE92/00055, Jan. 29, 1992, Pat. No. 5,674,861.

[30] Foreign Application Priority Data

Feb. 4, 1991 [SE] Sweden .................................. 9100341

[51] Int. Cl.$^6$ .............................. C07J 71/00; A61K 31/58
[52] U.S. Cl. ............................................. 514/174; 540/70
[58] Field of Search ................................ 540/70; 514/174

[56] References Cited

U.S. PATENT DOCUMENTS

| | | | |
|---|---|---|---|
| 3,928,326 | 12/1975 | Brattsand et al. | 260/239.55 |
| 4,404,200 | 9/1983 | Thalen et al. | 424/241 |
| 4,695,625 | 9/1987 | Macdonald | 540/63 |
| 4,835,145 | 5/1989 | MacDonald | 514/174 |
| 5,614,514 | 3/1997 | Axelsson et al. | 514/174 |
| 5,674,861 | 10/1997 | Andersson et al. | 514/174 |

OTHER PUBLICATIONS

Thalen et al., Acta Pharm. Suec. (1984), 21(2), 109–24.
Thalen et al., Acta. Pharm. Suec. (1987), 24, 97–114.
Andersson et al. Xenobiotica (1987), 17(1), 35–44.

Primary Examiner—Richard L. Raymond
Assistant Examiner—Bruck Kifle
Attorney, Agent, or Firm—White & Case L.L.P.

[57] ABSTRACT

Disclosed are processes for preparing the 22R and 22S epimers of the compound

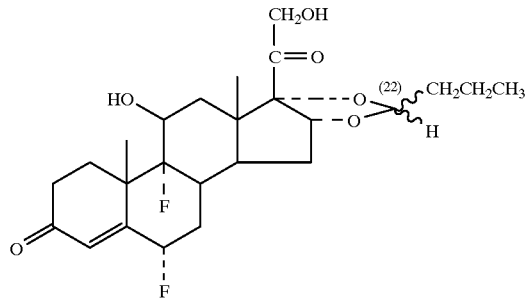

The processes involve acetalization, transacetalization, hydrolysis (of an ester) or hydrogenation (of a diene) of an appropriate starting material. Also disclosed are pharmaceutical compositions comprising the compounds produced by the processes and methods of treatment of inflammatory and allergic conditions employing the compounds.

7 Claims, No Drawings

PROCESSES FOR THE PRODUCTION OF ANTI-INFLAMMATORY STEROIDS

This application is a continuation of application Ser. No. 08/094,207, filed on Aug. 31, 1993 U.S. Pat. No. 5,674,861.

FIELD OF THE INVENTION

The present invention relates to novel anti-inflammatory and anti-allergic active compounds and to processes for their preparation. The invention also relates to pharmaceutical compositions containing the compounds and to methods of the pharmacological use of the compounds.

The object of the invention is to provide an anti-inflammatory, immunosupressive and anti-allergic glucocorticosteroid or a pharmaceutical composition thereof with high activity at the application place, e.g. in the respiratory tract, on the skin, in the intestinal tract, in the joints or in the eye directing the drug to a delimited target area, thereby inducing low glucocorticoid systemic effects.

BACKGROUND ART

It is known that glucocorticosteroids (GCS) can be used for local therapy of inflammatory, allergic or immunologic diseases in respiratory airways (e.g. asthma, rhinitis), in skin (eczema, psoriasis) or in bowel (ulcerative colitis, Morbus Crohn). With local glucocorticosteroid therapy, clinical advantages over general therapy (with e.g. glucocorticosteroid tablets) are obtained, especially regarding reduction of the unwanted glucocorticoid effects outside the diseased area due to reduction of the necessary dose. To reach even higher clinical advantages, in e.g. severe respiratory airway disease, GCS must have a suitable pharmacological profile. They should have high intrinsic glucocorticoid activity at the application site but also a rapid inactivation before or after uptake into the general circulation.

DISCLOSURE OF THE INVENTION

One object of the invention is to describe new GCS compounds. They are characterized by high anti-inflammatory, immunosupressive and anti-anaphylactic potency at the application site and particularly they have a markedly improved relationship between that potency and the activity to provoke GCS actions outside the treated region.

The compounds of the invention are a 22R or 22S epimer of a compound of the general formula

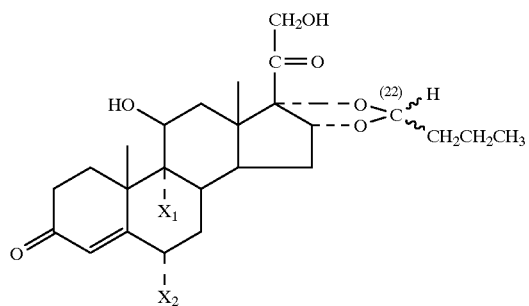

I wherein $X_1$ and $X_2$ are the same or different and each represents a hydrogen atom or a fluorine atom, provided that $X_1$ and $X_2$ are not simultaneously a hydrogen atom.

The individual 22R and 22S epimers of the formula (I) can be elucidated in the following way due to the chirality at the carbon atom in 22-position:

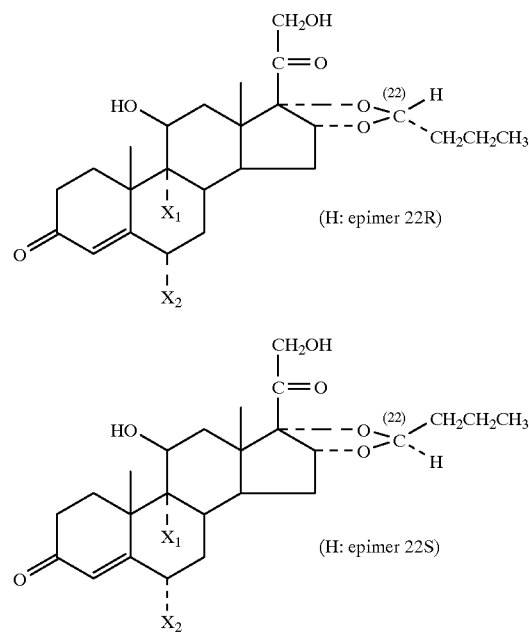

wherein $X_1$ and $X_2$ are as defined above.

An epimer 22R and 22S, respectively, of formula I above is by definition a compound containing not more than 2 per cent by weight, preferably not more than 1 per cent by weight of the other epimer.

The preferred compounds of the invention are the 22R and 22S epimers of the structure

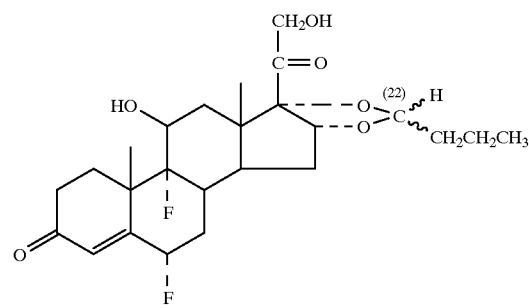

The preferred steroid has the R configuration at the 22 carbon atom.

Methods of Preparation

The 16α,17α-acetals of the formula I are prepared by reaction of a compound with the formula

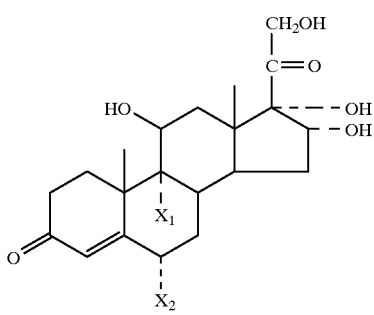

wherein $X_1$ and $X_2$ have the above given definition, with an aldehyde of the formula

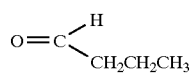

The reaction is carried out by adding the steroid to a solution of the aldehyde together with an acid catalyst, e.g. perchloric acid, p-toluenesulfonic acid, hydrochloric acid in an ether, preferably dioxane or in acetonitrile.

The compounds of the formula I are also prepared by transacetalisation of the corresponding 16α, 17α-acetonides

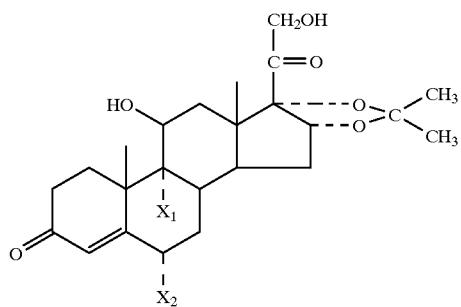

wherein $X_1$ and $X_2$ have the above given definition, with an aldehyde of the formula

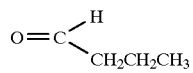

The reaction is carried out by adding the steroid to a solution of the aldehyde together with an acid catalyst, e.g. perchloric acid, p-toluenesulfonic acid, hydrochloric acid in an ether, preferably dioxane, or in acetonitrile.

The reaction can also be performed in a reaction medium which is a hydrocarbon, preferably isooctane, wherein the solubility of the pregnane derivative (the 16,17-acetonide or the 16,17-diol) is less than 1 mg/l, or in a halogenated hydrocarbon, preferably methylene chloride or chloroform.

The reaction is catalysed by a hydrohalogen acid or an organic sulfonic acid such as p-toluenesulfonic acid.

The reaction is performed in the presence of small grains of an inert material, such as glass, ceramic, sifted silicone dioxide (sand) or inert metal particles, such as granulated stainless steel or tantalum in the reaction medium (when the reaction is performed in a hydrocarbon solvent).

The 22R-epimer is so exclusively obtained that it can be sufficiently purified to be used as a pharmaceutical substance by recrystallization instead of by the more expensive chromatographic procedure.

At the reaction procedure in hydrocarbons the steroid-catalyst complex will form a big sticky lump which makes stirring and effective reaction impossible.

To overcome this small grains of an inert material and effective stirring is used to prevent the formation of a big lump and instead divide the steroid-catalyst complex into a thin layer around the grains. Thereby, the reactive surface will be much larger and the reaction with the carbonyl compound proceeds very rapidly.

The inert grain material used in the process, preferably silicon dioxide ($SiO_2$), should consist of free-flowing small particles. The particle size ranges from 0.1–1.01 mm, preferably 0.1–0.3 mm used in the reaction will range from 1:5 to 1:50, preferably 1:20.

By hydrohalogen acid is to be understood hydrofluoric, hydrochloric, hydrobromic and hydriodic acid and the corresponding oxohalogen acids, such as perchloric acid.

The individual 22R and 22S epimers, which are formed at the acetalisation, possess practically identical solubility characteristics. Accordingly, they have turned out to be impossible to separate and isolate from the epimeric mixture by conventional methods for resolution of stereoisomers, e.g. fractional crystallization. In order to obtain the individual epimers separately, the stereoisomeric mixtures according to the formula I above are subject to column chromatography, thus separating the 22R and 22S epimers in view of different mobility on the stationary phase. The chromatography may be carried out for instance on cross-linked dextran gels of the type Sephadex LH, e.g. Sephadex LH-20 in combination with a suitable organic solvent as eluting agent. Sephadex LH-20, prepared by Pharmacia Fine Chemicals AB, Uppsala, Sweden, is a beadformed hydroxypropylated dextran gel wherein the dextran chains are cross-linked to give a three-dimensional polysaccharide network. As mobile phase, halogenated hydrocarbons, e.g. chloroform or a mixture of heptane-chloroform-ethanol in the proportions 0–50:50–100:10–1, has successfully been used, preferably a 20:20:1 mixture.

Alternatively, the chromatography may be carried out on microparticulate bonded phase columns, e.g. 10 μm octadecylsilane (μBondapak $C_{18}$) or μBondapak CN columns in combination with a suitable organic solvent as mobile phase. Ethanol water mixtures in the proportions 40–60:60–40 have successfully been used.

The epimers 22R and 22S can also be obtained from a steroisomeric mixture with the general formula

IV

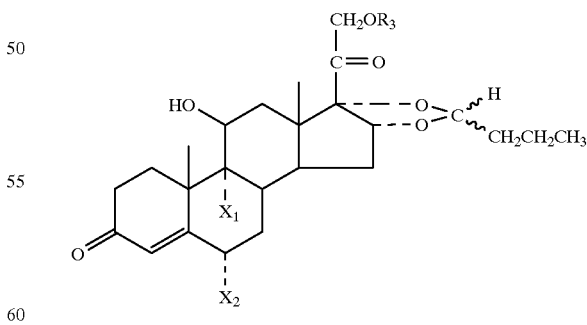

wherein $X_1$ and $X_2$ have the above given definition and $R_3$ is a carboxylic acid residue having a straight hydro-carbon chain having 1–5 carbon atoms preferably the 21-acetate, after resolution by chromatography on Sephadex LH-20 together with a suitable solvent or mixture of solvents, e.g. heptane-chloroform-ethanol in the proportions 0–50:50–10:10–1, preferably 20:20:1, as mobile phase. The separated and isolated epimers 22R and 22S with the general formula (IV) above are submitted to base catalyzed hydrolysis with hydroxides, carbonates or hydrogen carbonates of alkaline metals, e.g. sodium or potssium hydroxide, sodium or potassium carbonate or sodium or potassium hydrogen carbonate to give the epimers 22R and 22S of the formula II and III respectively, above. The hydrolysis can alternatively be performed with an acid as catalyst, e.g. hydrochloric acid or sulfuric acid.

The compounds of the formula IV are prepared according to methods described in the companion application no (our case D 1093-1 SE).

Pharmaceutical Preparations

The compounds of the invention may be used for different modes of local administration dependent on the site of inflammation, e.g. percutaneously, parenterally or for local administration in the respiratory tract by inhalation. An important aim of the formulation design is to reach optimal bioavailability of the active steroid ingredient. For percutaneous formulations this is advantagenously achieved if the steroid is dissolved with a high thermodynamic activity in the vehicle. This is attained by using a suitable system or solvents comprising suitable glycols, such as propylene glycol or 1,3-butandiol either as such or in combination with water.

It is also possible to dissolve the steroid either completely or partially in a lipophilic phase with the aid of a surfactant as a solubilizer. The percutaneous compositions can be an ointment, an oil in water cream, a water in oil cream or a lotion. In the emulsion vehicles the system comprising the dissolved active component can make up the disperse phase as well as the continuous one. The steroid can also exist in the above compositions as a micronized, solid substance.

Pressurized aerosols for steroids are intended for oral or nasal inhalation. The aerosol system is designed in such a way that each delivered dose contains 10–1000 $\mu$g, preferably 20–250 $\mu$g of the active steroid. The most active steroids are administered in the lower part of the dose range. The micronized steroid consists of particles substantially smaller than 5 $\mu$m, which are suspended in a propellent mixture with the assistance of a dispersant, salt of dioctylsulphosuccinic acid.

The steroid can also be administered by means of a dry powder inhaler.

One possibility is to mix the micronized steroid with a carrier substance such as lactose or glucose. The powder mixture is dispensed into hard gelatin capsules, each containing the desired dose of the steroid. The capsule is then placed in a powder inhaler and the dose is inhaled into the patient's airways.

Another possibility is to process the micronized powder into spheres which-break up during the dosing procedure. This spheronized powder is filled into the drug reservoir in a multidose inhaler, e.g. Turbuhaler. A dosing unit meters the desired dose which is then inhaled by the patient. With this system the steroid without a carrier substance is delivered to the patient.

The steroid can also be included in formulations intended for treating inflammatory bowel diseases, either by the oral route or rectally. Formulations for the oral route should be constructed so that the steroid is delivered to the inflamed parts of the bowel. This can be accomplished by different combinations of enteric and/or slow or control release principles. For the rectal route an enema type formulation is suitable.

WORKING EXAMPLES

The invention will be further illustrated by the following non-limitative examples. In the examples a flow-rate of 2.5 ml/cm$^2$·h$^{-1}$ is used at the preparative chromatographic runs. Molecular weights are in all examples determined with chemical ionization mass spectrometry (CH$_4$ as reagent gas) and the melting points on a Leitz Wetzlar hot stage microscope. The HPLC analyses (High Performance Liquid Chromatography) have been performed on a $\mu$Bondapak C$_{18}$ column (300×3.9 mm i.d.) with a flow rate of 1.0 ml/min and with ethanol/water in-ratios between 40:60 and 60:40 as mobile phase, if not otherwise stated.

Example 1

6$\alpha$,9$\alpha$-Difluoro-11$\beta$,16$\alpha$,17$\alpha$,21-tetrahydroxypregn-4-ene-3,20-dione.

A solution of 6$\alpha$, 9$\alpha$-difluoro-16$\alpha$-hydroxyprednisolone (2.0 g) in 1000 ml of absolute ethanol was added to a solution of tris(triphenylphosphine)rhodium chloride (2.2 g) in 500 ml of toluene and hydrogenated at room temperature and atmospheric pressure for 7 days. The reaction mixture was evaporated to dryness and methylene chloride (50 ml) was added. The solid precipitate was collected and repeatedly washed with small portions of methylene chloride to give 1.8 g of 6$\alpha$,9$\alpha$-difluoro-11$\beta$,16$\alpha$,17$\alpha$,21-tetrahydroxypregn-4-ene-3,20-dione. Molecular weight 414 (calc. 414.5).

Example 2

6$\alpha$,9$\alpha$-Difluoro-11$\beta$,21-dihydroxy-16$\alpha$,17$\alpha$-[(1-methylethylidene)bis(oxv)]pregn-4-ene-3,20-dione A suspension of 0.9 g of tris(triphenylphosphine)rhodium chloride in 250 ml of degassed toluene was hydrogenated for 45 min at room temperature and atmospheric pressure. A solution of 1.0 g of fluocinolone 16$\alpha$,17$\alpha$-acetonide in 100 ml of absolute ethanol was added and the hydrogenation was continued for another 40 h. The reaction product was evaporated and the residue purified by flash chromatography on silica using acetone-petroleum ether as mobile phase to remove the main part of the catalyst. The eluate was evaporated and the residue further purified by chromatography on a Sephadex LH-20 column (72.5×6.3 cm) using chloroform as mobile phase. The fraction 3555–4125 ml was collected and evaporated yielding 0.61 g of 6$\alpha$,9$\alpha$-difluoro-11$\beta$,21-dihydroxy-16$\alpha$,17$\alpha$-[(1-methylethylidene)-bis(oxy)]pregn-4-ene-3,20-dione. Melting point 146–151° C. $[\alpha]_D^{25}$=+124.5° (c=0.220;CH$_2$Cl$_2$). Molecular weight 454 (calc. 454.6). Purity: 98.5% (HPLC-analysis).

Example 3

(22RS)-16$\alpha$,17$\alpha$-Butylidenedioxy-6$\alpha$,9$\alpha$-difluoro-11$\beta$,21-dihydroxypregn-4-ene-3,20-dione.

To a solution of freshly distilled butanal (0.5 g) and 0.4 ml of perchloric acid (70%) in 100 ml of purified and dried dioxane, 1.8 g of 6$\alpha$,9$\alpha$-difluoro-11$\beta$,16$\alpha$,17$\alpha$,21-tetrahydroxypregn-4-ene-3,20-dione was added in small portions with stirring during 30 min. The reaction mixture was stirred at room temperature for another 5 h. Methylene chloride (600 ml) was added and the solution was washed with aqueous potassium carbonate and water, and dried over anhydrous magnesium sulfate. The crude product obtained after evaporation was purified by chromatography on a Sephadex LH-20 column (76×6.3 cm) using chloroform as mobile phase. The fraction 3015-3705 ml was collected and evaporated leaving 1.5 g of (22RS)-16$\alpha$,17$\alpha$-butylidenedioxy-6$\alpha$,9$\alpha$-difluoropregn-4-ene-3,20-dione. Molecular weight 468 (calc.468.5).

Example 4

(22R)-16α, 17α-Butylidenedioxy-6α, 9α-difluoro-11β,21-dihydroxypregn-4-ene-3,20-dione.

6α, 9α-Difluoro-11β,21-dihydroxy-16α, 17α-[(1-methylethylidene)bis(oxy)]pregn-4-ene-3,20-dione (100 mg), 0.03 ml of butanal, 2 ml of fine sand (SiO$_2$) and 4 ml of heptane were mixed at room temperature. Perchloric acid (70%; 0.1 ml) was added under vigorous stirring. The reaction mixture was stirred at room temperature for another 5 h, cooled and filtered. The solid residue was washed with 4×15 ml of aqueous potassium carbonate (10%) followed by 4×15 ml of water and then stirred 4 times with 25 ml of dichloromethane. The combined extracts were washed with water, dried and evaporated. The residue was dissolved in a small amount of dichloromethane and precipitated with petroleum ether (b.p. 40–60° C.) yielding 75 mg of (22R)-16α, 17α-butylidenedioxy-6α,9α-difluoro-11β,21-dihydroxypregn-4-ene-3,20-dione mixed with 3% of the (22S)-epimer. The purity determined by HPLC analysis was 98%. Molecular weight 468 (calc. 468.5).

Example 5

(22R)- and (22S)-16α,17α-Butylidenedioxy-6α,9α-difluoro-11β,21-dihydroxypregn-4-ene-3,20-dione.

(22RS) -16α,17α-Butylidenedioxy-6α,9α-difluoro-11β, 21-dihydroxypregn-4-ene-3,20-dione (1.5 g) was resolved into its 22R- and 22S-epimers by chromatography on a Sephadex LH-20 column (76×6.3 cm) using a n-heptane-chloroform-ethanol (20:20:1) mixture as mobile phase. The fractions 1845–2565 ml (A) and 2745–3600 ml (B) were collected and evaporated. The two products were precipitated from methylene chloride—petroleum ether. The product from fraction A (332 mg) was identified with $^1$H-NMR and mass spectrometry to be (22S)-16α,17α-butylidenedioxy-6α,9α-difluoro-11β,21-dihydroxypregn-4-ene-3,20-dione and the product from the B fraction (918 mg) as the 22R-epimer.

The epimers had the following properties. Epimer 22S: Melting point 231–44° C.; $[\alpha]_D^{25}$=+84.4° (c=0.096; CH$_2$Cl$_2$); molecular weight 468 (calc. 468.5). Epimer 22R: Melting point 150–56° C.; $[\alpha]_D^{25}$=+120.0° (c=0.190; CH$_2$Cl$_2$); molecular weight 468 (calc. 468.5). The purity of the epimers was determined by HPLC-analysis to be 95.7% for the 22S-epimer (containing 1,2% of the 22R-epimer) and 98.8% for the 22R-epimer (containing 0,7% of the 22S-epimer).

Example 6

(22R)-16α,17α-butylidenedioxy-6α,9α-difluoro-11β,21-dihydroxypregn-4-ene-3-20-dione.

A solution of (22R)-16α,17α-butylidenedioxy-6α,9α-difluoro-11β,21-dihydroxypregna-1,4-diene-3,20-dione (4.0 g) and tris(triphenylphosphine)rhodium chloride (0.40g) in 150 ml of absolute ethanol was hydrogenated at room temperature for 68 h. Water (150 ml) was added and the mixture filtered through a HV LP 0,45 μm filter. The filtrate was partially evaporated. The precipitate formed was filtered leaving 1.48 g of crude product which was purified on a Sephadex LH-20 column (75×6.3 cm) using chloroform as mobile phase. The fraction 3600–4200 ml was collected and evaporated and further purified on a Sephadex LH-20 column (75×6.3 cm) using heptane:chloroform:ethanol, 20:20:1, as mobile phase. The fraction 9825–10500 ml was collected and evaporated yielding 0.57 g of (22R)-16α,17α-butylidenedioxy-6α,9α-difluoro-11β,21-dihydroxypregn-4-ene-3,20-dione. Molecular weight 468 (calc. 468.5). Purity: 96.5% (HPLC-analysis).

Another 220 ml of water was added to the filtrate above giving a further portion of solid product which after purification on a Sephadex LH-20 column (75×6.3 cm) using chloroform as mobile phase (fraction 3795–4275 ml) yielded 1.04 g of (22R)-16α,17α-butylidenedioxy-6α,9 -difluoro-11β,21-dihydroxypregn-4-ene-3,20-dione. Molecular weight 468 (calc 468.5). Purity 98.3% (HPLC-analysis).

Example 7

6α-Fluoro-11β,16α,17α,21-tetrahydroxypregn-4-ene-3,20-dione.

To a suspension of 1.4 g of tris(triphenylphosphine)-rhodium chloride in 300 ml of toluene was added a solution of 1170 mg of 6α-fluoro-11β,16α,17α,21-tetrahydroxypregna-1,4-diene-3,20-dione in 250 ml of absolute ethanol. The mixture was hydrogenated 22 h at room temperature and atmospheric pressure and evaporated. The residue was precipitated from acetone-chloroform yielding 661 mg of 6α-fluoro-11β,16α,17α,21-tetrahydroxypregn-4-ene-3,20-dione. Molecular weight 396 (calc. 396.5). Purity: 96.6% (HPLC-analysis).

Example 8

(22RS) -16α,17α-Butylidenedioxy-6α-fluoro-11β,21-dihydroxypregn-4-ene-3,20-dione 6α-Fluoro-11β,16α,17α,21-tetrahydroxypregn-4-ene-3, 20-dione (308 mg) was added in portions to a solution of butanal (115 mg) and 70% perchloric acid (0.2 ml) in 50 ml of dioxane. The reaction mixture was stirred at room temperature for 6 h. Methylene chloride (200 ml) was added and the solution washed with 10% aqueous potassium carbonate and water and dried. The residue after evaporation was purified on a Sephadex LH-20 column (87×2.5 cm) using chloroform as mobile phase. The fraction 420–500 ml was collected and evaporated yielding 248 mg of (22RS)-16α, 17α-butylidenedioxy-6α-fluoro-11β,21-dihydroxypregn-4-ene-3,20-dione. Melting point 85–96° C. $[\alpha]_D^{25}$ =+119.8° (c=0.192; CH$_2$Cl$_2$). Molecular weight 450 (calc. 450.6). Purity: 96.1% (HPLC-analysis). The distribution between the 22R- and 22S-epimers was 59/41 (HPLC-analysis).

Example 9

(22R)- and (22S)-Butylidenedioxy-6α-fluoro-11β,21-dihydroxypregn-4-ene-3,20-dione (22RS) -16α,17α-Butylidenedioxy-6α-fluoro-11β,21-dihydroxypregn-4-ene-3,20-dione (225 mg) was resolved by preparative HPLC in portions on a μBondapak C$_{18}$ column (150×19 mm) using ethanol:water, 40:60, as mobile phase. The fractions centered at 265 ml (A) and 310 ml (B), respectively were collected and evaporated. After precipitation from methylene chloride—petroleum ether fraction A yielded 68 mg of (22R)-16α,17α-butylidenedioxy-6α-fluoro-11β,21-dihydroxypregn-4-ene-3,20-dione. Melting point 180–192° C. $[\alpha]_D^{25}$=+138.9° (c=0.144; CH$_2$Cl$_2$). Molecular weight 450 (calc. 450.6). Purity: 99.4% (HPLC-analysis).

Fraction B gave after precipitation 62 mg of (22S)-16α, 17α-butylidenedioxy-6α-fluoro-11β,21-dihydroxypregn-4-ene-3,20-dione. Melting point 168–175° C. $[\alpha]_D^{25}$=+103.7° (c=0.216; CH$_2$Cl$_2$). Molecular weight 450 (calc. 450.6). Purity: 99.5% (HPLC-analysis).

Example 10

(22R)- and (22S)-21-Acetoxy-16α,17α-butylidenedioxy-6α-fluoro-11β-hydroxypregn-4-ene-3,20-dione (22RS)-16α,17α-Butylidenedioxy-6α-fluoro-11β,21-dihydroxypregn-4-ene-3,20-dione (68 mg) was dissolved in 1 ml of pyridine. Acetic anhydride (1 ml) was added and the reaction mixture stirred at room temperature for 1 h, poured into ice-water and extracted with 3×25 ml of methylene chloride. The extract was dried and evaporated. The residue was chromatographed on a Sephadex LH-20 column (89× 2.5 cm) using heptane:chloroform:ethanol, 20:20:1, as mobile phase. The fractions 380–400 ml (A) and 420–440 ml (B) were collected and evaporated.

After precipitation from methylene chloride—petroleum ether fraction A yielded 14 mg of (22S)-21-acetoxy-16α, 17α-butylidenedioxy-6α-fluoro-11β-hydroxypregn-4-ene-3,20-dione. Melting point 179–186° C. $[\alpha]_D^{25}=+86.2°$ (c=0.188; $CH_2Cl_2$). Molecular weight 492 (calc. 492.6). Purity: 97.5% (HPLC-analysis).

Fraction B gave after precipitation 20 mg of (22R)-21-acetoxy-16α,17α-butylidenedioxy-6α-fluoro-11β-hydroxypregn-4-ene-3,20-dione. Melting point 169–172° C. $[\alpha]_D^{25}=+139.0°$ (c=0.200; $CH_2Cl_2$). Molecular weight 492 (calc. 492.6). Purity: 97.9% (HPLC-analysis).

Example 11

(22R)-16α,17α-Butylidenedioxy-6α-fluoro-11β,21-dihydroxypregn-4-ene-3,20-dione.

To a solution of 20 mg of (22R)-21-acetoxy-16α,17α-butylidenedioxy-6α-fluoro-11β-hydroxypregn-4-ene-3,20-dione in 2 ml of ethanol, 2 ml of 2M hydrochloric acid was added. After stirring at 60° C. for 5 h the reaction mixture was neutralized with saturated aqueous sodium hydrogen carbonate and extracted with 3×25 ml of methylene chloride. The combined extracts were washed with water, dried and evaporated. The residue was purified on a Sephadex LH-20 column (87×2.5 cm) using chloroform as mobile phase. The fraction 460–515 ml was collected and evaporated yielding 8 mg of (22R)-16α,17α-butylidenedioxy-6α-fluoro-11β,21-dihydroxypregn-4-ene-3,20-dione. Molecular weight 450 (calc. 450.6). Purity 98.4% (HPLC-analysis).

Example 12

(22S)-16α,17α-Butylidenedioxy-6α-fluoro-11β,21-dihydroxypregn-4-ene-3,20-dione.

To a solution of 14 mg of (22S)-21-acetoxy-16α,17α-butylidenedioxy-6α-fluoro-11β,-hydroxypregn-4-ene-3,20-dione in 2 ml of ethanol, 2 ml of 2M hydrochloric acid was added. The reaction, isolation and purification was performed in the same way as in Example 11. The fraction 455–510 ml was collected and evaporated giving 7 mg of (22S)-16α,17α-butylidenedioxy-6α-fluoro-11β,21-dihydroxypregn-4-ene-3,20-dione. Molecular weight 450 (calc. 450.6). Purity: 98.6% (HPLC-analysis).

Example 13

9α-Fluoro-11β,16α,17α,21-tetrahydroxypregn-4-ene-3,20-dione

A suspension of 3.0 g of tris(triphenylphosphine)rhodium chloride in 1000 ml of degassed toluene was hydrogenated for 45 min at room temperature and atmospheric pressure. A solution of 5.0 g of triamcinolone in 500 ml of absolute ethanol was added and the hydrogenation was continued for 48 h. The reaction mixture was evaporated to dryness and suspended in 50 ml of methylene chloride. After filtration the solid phase was repeatedly washed with small portions of methylene chloride and yielded after drying 4.4 g of 9α-fluoro-11β,16α,17α,21-tetrahydroxypregn-4-ene-3,20-dione. Molecular weight 396 (calc. 396.5).

Example 14

(22RS)-16α,17α-Butylidenedioxy-9α-fluoro-11β,21-dihydroxypregn-4-ene-3,20-dione

To a solution of freshly distilled butanal (100 mg) and 0.2 ml of perchloric acid (70%) in 50 ml of purified and dried dioxane 9α-fluoro-11β,16α,17α,21-tetrahydroxypregn-4-ene-3,20-dione (340 mg) was added in small portions with stirring during 20 min. The reaction mixture was stirred at room temperature for another 5 h. Methylene chloride (200 ml) was added and the solution was washed with aqueous potassium carbonate and water and dried over anhydrous magnesium sulfate. The crude product obtained after evaporation was purified on a Sephadex LH-20 column (72.5×6.3 cm) using chloroform as mobile phase. The fraction 2760–3195 ml was collected and evaporated yielding 215 mg of (22RS)-16α,17α-butylidenedioxy-9α-fluoro-11β,21-dihydroxypregn-4-ene-3,20-dione. Molecular weight 450 (calc.450.6). Purity 97.4% (HPLC-analysis).

Example 15

(22R)-and (22S)-16α,17α-Butylidenedioxy-9α-fluoro-11β, 21-dihydroxypregn-4-ene-3,20-dione.

(22RS)-16α,17α-Butylidenedioxy-9α-fluoro-11β,21-dihydroxypregn-4-ene-3,20-dione (200 mg) was resolved by chromatography on a Sephadex LH-20 column (76×6.3 cm) using a heptane-chloroform-ethanol (20:20:1) mixture as mobile phase. The fractions 7560–8835 ml (A) and 8836–9360 ml (B) were collected and evaporated. The product from fraction A (128 mg) was identified with $^1$H-NMR and mass spectrometry to be (22S)-16α,17α-butylidenedioxy-9α-fluoro-11β,21-dihydr-oxypregn-4-ene-3,20-dione and the product from the B fraction (50 mg) as the 22R-epimer.

The epimers had the following properties. Epimer 22S: Melting point 180–190° C.; $[\alpha]_D^{25}=+105.6°$ (c=0.214;$CH_2Cl_2$); molecular weight 450 (calc. 450.6). Epimer 22R: Melting point 147–151° C; $[\alpha]_D^{25}=+133.7°$ (C=0.196;$CH_2Cl_2$); molecular weight 450 (calc. 450.6). The purity of the epimers was determined by HPLC-analysis to be 97.6% for the 22S-epimer (containing 1,8% of the 22R-epimer) and 98.2% for the 22R-epimer (containing 0,8% of the 22S-epimer).

Example 16

Pharmaceutical Preparations

The following non-limitative examples illustrate formulations intended for different topical forms of administration. The amount of active steroid in the percutaneous formulations are ordinarily 0.001–0.2% (w/w), preferably 0.01–0.1% (w/w).

Formulation 1, Ointment

| Steroid, micronized | | 0.025 g |
| Liquid paraffin | | 10.0 g |
| White soft paraffin | ad | 100.0 g |

Formulation 2, Ointment

| Steroid | | 0.025 g |
| Propylene glycol | | 5.0 g |
| Sorbitan sesquioleate | | 5.0 g |
| Liquid paraffin | | 10.0 g |
| White soft paraffin | ad | 100.0 g |

Formulation 3, Oil in Water Cream

| | | |
|---|---|---|
| Steroid | | 0.025 g |
| Cetanol | | 5.0 g |
| Glyceryl monostearate | | 5.0 g |
| Liquid paraffin | | 10.0 g |
| Cetomacrogol 1000 | | 2.0 g |
| Citric acid | | 0.1 g |
| Sodium citrate | | 0.2 g |
| Propylene glycol | | 35.0 g |
| Water | ad | 100.0 g |

Formulation 4, Oil in Water Cream

| | | |
|---|---|---|
| Steroid, micronized | | 0.025 g |
| White soft paraffin | | 15.0 g |
| Liquid paraffin | | 5.0 g |
| Cetanol | | 5.0 g |
| Sorbimacrogol stearate | | 2.0 g |
| Sorbitan monostearate | | 0.5 g |
| Sorbic acid | | 0.2 g |
| Citric acid | | 0.1 g |
| Sodium citrate | | 0.2 g |
| Water | ad | 100.0 g |

Formulation 5, Water in Oil Cream

| | | |
|---|---|---|
| Steroid | | 0.025 g |
| White soft paraffin | | 35.0 g |
| Liquid paraffin | | 5.0 g |
| Sorbitan sesquioleate | | 5.0 g |
| Sorbic acid | | 0.2 g |
| Citric acid | | 0.1 g |
| Sodium citrate | | 0.2 g |
| Water | ad | 100.0 g |

Formulation 6, Lotion

| | | |
|---|---|---|
| Steroid | | 0.25 mg |
| Isopropanol | | 0.5 ml |
| Carboxyvinylpolymer | | 3 mg |
| NaOH | | q.s. |
| Water | ad | 1.0 g |

Formulation 7, Suspension for Injection

| | | |
|---|---|---|
| Steroid, micronized | | 0.05–10 mg |
| Sodium carboxymethylcellulose | | 7 mg |
| NaCl | | 7 mg |
| Polyoxyethylene (20) sorbitan monooleate | | 0.5 mg |
| Phenyl carbinol | | 8 mg |
| Water, sterile | ad | 1.0 ml |

Formulation 8, Aerosol for Oral and Nasal Inhalation

| | |
|---|---|
| Steroid, micronized | 0.1% w/w |
| Sorbitan trioleate | 0.7% w/w |
| Trichlorofluoromethane | 24.8% w/w |
| Dichlorotetrafluoromethane | 24.8% w/w |
| Dichlorodifluoromethane | 49.6% w/w |

Formulation 9, Solution for Atomization

| | | |
|---|---|---|
| Steroid | | 7.0 mg |
| Propylene glycol | | 5.0 g |
| Water | ad | 10.0 g |

Formulation 10, Powder for Inhalation

A gelatin capsule is filled with a mixture of

| | |
|---|---|
| Steroid, micronized | 0.1 mg |
| Lactose | 20 mg |

The powder is inhaled by means of an inhalation device.

Formulation 11, Powder for Inhalation

The spheronized powder is filled into a multidose powder inhaler. Each dose contains

| | |
|---|---|
| Steroid, micronized | 0.1 mg |

Formulation 12, Powder for Inhalation

The spheronized powder is filled into a multidose powder inhaler. Each dose contains

| | |
|---|---|
| Steroid, micronized | 0.1 mg |
| Lactose, micronized | 1 mg |

Formulation 13, Capsule for Treating the Small Bowel

| | |
|---|---|
| Steroid | 1.0 mg |
| Sugar spheres | 321 mg |
| Aquacoat ECD 30 | 6.6 mg |
| Acetyltributyl citrate | 0.5 mg |
| Polysorbate 80 | 0.1 mg |
| Eudragit L100-55 | 17.5 mg |
| Triethylcitrate | 1.8 mg |
| Talc | 8.8 mg |
| Antifoam MMS | 0.01 mg |

Formulation 14, Capsule for Treating the Large Bowel

| | |
|---|---|
| Steroid | 2.0 mg |
| Sugar spheres | 305 mg |
| Aquacoat ECD 30 | 5.0 mg |
| Acetyltributyl citrate | 0.4 mg |
| Polysorbate 80 | 0.14 mg |
| Eudragit NE30 D | 12.6 mg |
| Eudragit S100 | 12.6 mg |
| Talc | 12.6 mg |

Formulation 15, Rectal Enema

| | | |
|---|---|---|
| Steroid | | 0.02 mg |
| Sodium carboxymethylcellulose | | 25 mg |
| Disodium edetate | | 0.5 mg |
| Methyl parahydroxybenzoate | | 0.8 mg |
| Propyl parahydroxybenzoate | | 0.2 mg |
| Sodium chloride | | 7.0 mg |
| Citric acid anhydrous | | 1.8 mg |
| Polysorbate 80 | | 0.01 mg |
| Water, purified | ad | 1.0 ml |

Pharmacology

The selectivity for local antiinflammatory activity can be exemplified by the following airway model. A considerable fraction of inhaled GCS is deposited in the pharynx and is subsequently swallowed ending up in the gut. This fraction contributes to the unwanted side effects of the steroid since it is acting outside the area intended for treatment (the lung). Therefore, it is favourable to use a GCS with high local anti-inflammatory activity in the lung but low GCS induced effects after oral uptake. Studies were therefore done in order to determine the GCS induced effects after local application in the lung as well as after peroral administration and the differentiation between glucocorticosteroid actions in the treated lung region and outside this area were tested in the following way.

Test models

A. Test model for desired local antiinflammatory activity on airway mucosa (left lung lobe)

Sprague Dawley rats (250 g) were slightly anaesthetized with Ephrane and the glucocorticosteroid test preparation (suspended in saline) in a volume of 0.5 ml/kg was instilled into just the left lung lobe. Two hours later a suspension of Sephadex (5 mg/kg in a volume of 1 ml/kg) was instilled under slight anaesthesia in the trachea well above the bifurcation so that the suspension reached both the left and right lung lobes. Twenty hours later the rats were killed and the left lung lobes dissected out and weighed. Control groups got saline instead of glucocorticosteroid preparation and saline instead of Sephadex suspension to determine the weight of non-drug treated Sephadex edema and the normal lung weight.

B. Test model for unwanted systemic effect by orally absorbed glucocorticosteroid Sprague Dawley rats (250 g) were slightly anaesthetized with Ephrane and after that the GCS test preparation in a volume of 0,5 ml/kg was given orally. Two hours later a suspension of Sephadex (5 mg/kg in a volume of 1 ml/kg) was instilled in the trachea well above the bifurcation so that the suspension reached both the left and the right lung lobes. Twenty hours later, the rats were killed and the lung lobes were weighed. Control groups got saline instead of glucocorticosteroid preparation and saline instead of Sephadex suspension to determine the weight of non-drug treated Sephadex edema and the normal weight.

The results of the comparative study are given in Table 1. The pharmacological profile of the tested compound of the invention was compared to that of budesonide. The results demonstrate that the compound according to example 6 shows a much higher local antiinflammatory activity than budesonide. Furthermore, the results also demonstrate a higher lung selectivity of the tested compound of the invention compared to the selected prior art compound since the dose required to inhibit lung edema ($ED_{50}$) by oral administration of the above mentioned compound is 32 times higher and of budesonide 13 times higher than the dose needed to inhibit lung edema by local application to the lung of the drugs. (Budesonide 4000 and 300 nmol/kg, example 6, 320 and 10 nmol/kg, respectively)

Thus it can be concluded that the compounds of the invention are well suited for local treatment of inflammatory disorders in the skin and various cavities of the body (e.g. lung, nose, bowel and joint).

TABLE 1

Effects of tested glucocorticosteroids in the Sephadex induced lung edema model in the rat. The results are given in relation to the corresponding control group given Sephadex

| Compound according to examples no | $ED_{50}$ (left lung administration; nmol/kg) Left lung lobe[x] | $ED_{50}$ (p.o. administration; nmol/kg) lung[x] |
|---|---|---|
| Budesonide | 300 | 4000 |
| 6 | 10 | 320 |

[x] $ED_{50}$ = required glucocorticosteroid dose to reduce the edema by 50%.

We claim:

1. A process for the preparation of a 22R or 22S epimer of a compound of the formula I

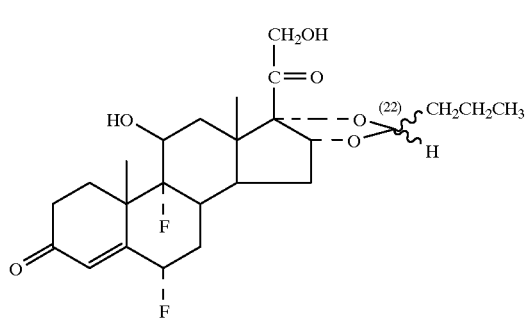

which comprises (a) reaction of a compound of the formula

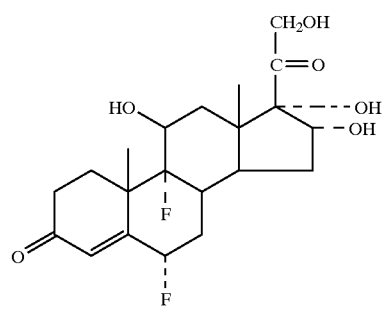

with an aldehyde of the formula
$HCOCH_2CH_2CH_3$, the reaction being carried out in the presence of a hydrohalogen acid or organic sulfonic acid catalyst in a reaction medium selected from the group consisting of an ether and acetonitrile, and whereafter the epimeric mixture is resolved into its stereoisomeric components; or (b) reaction of a compound of the formula

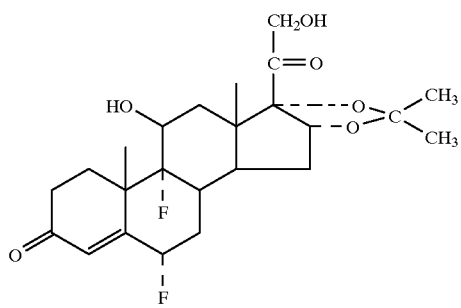

with an aldehyde of the formula

HCOCH₂CH₂CH₃, the reaction being carried out in the presence of a hydrohalogen acid or organic sulfonic acid catalyst in a reaction medium selected from the group consisting of an ether, acetonitrile, a hydrocarbon and a halogenated hydrocarbon, and whereafter the epimeric mixture is resolved into its stereoisomeric components; or (c) hydrolysis of a compound of the formula

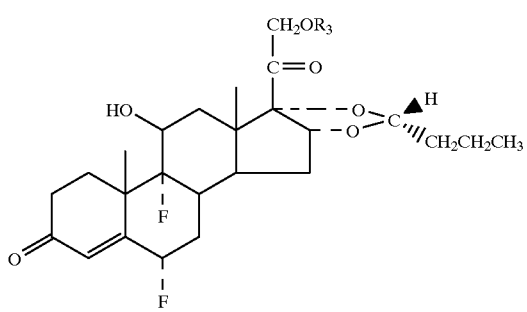

or

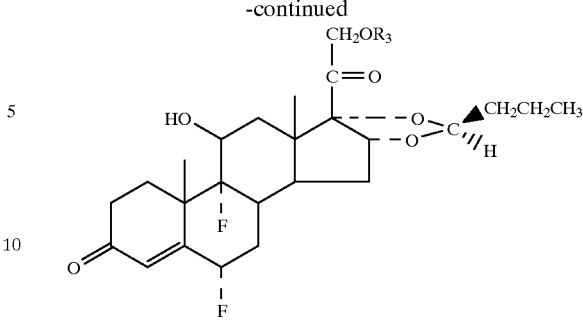

wherein $R_3$ is a carboxylic acid residue having a straight hydrocarbon chain of 1–5 carbon atoms; or (d) hydrogenation of a compound of the formula

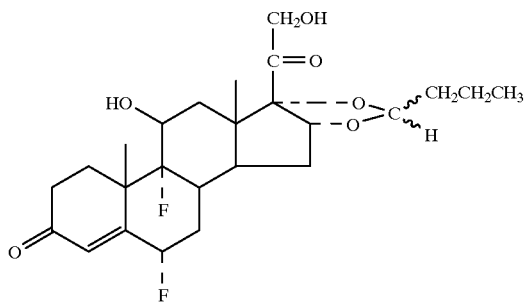

2. A process according to claim 1 for the preparation of a compound wherein the stereoisomeric configuration at the 22 carbon atom is R.

3. A pharmaceutical composition comprising as active ingredient a compound prepared by the process according to claim 2 or 1.

4. A pharmaceutical composition according to claim 3 in dosage unit form.

5. A pharmaceutical composition according to claim 3 comprising the active ingredient in association with a pharmaceutically acceptable carrier.

6. A pharmaceutical composition according to claim 4 comprising the active ingredient in association with a pharmaceutically acceptable carrier.

7. A method for treatment of inflammatory and allergic conditions in mammals, which comprises the administration to a host in need of such treatment of an effective amount of a compound prepared by a process according to claim 2 or 1.

* * * * *

UNITED STATES PATENT AND TRADEMARK OFFICE
CERTIFICATE OF CORRECTION

PATENT NO. : 5,939,409
DATED : August 17, 1999
INVENTOR(S) : Andersson, et al.

It is certified that error appears in the above-identified patent and that said Letters Patent is hereby corrected as shown below:

Col. 1, line 5, insert --, which was the National Stage of International Application No. PCT/SE92/00055, filed on Jan. 29, 1992, -- between "08/094,207, filed on Aug. 31, 1993" and "U.S. Pat. No. 5,674,861."

Col. 16, lines 18-30, delete

"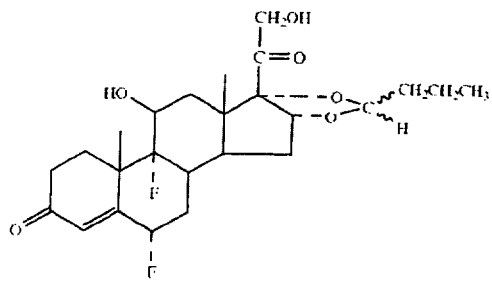"

UNITED STATES PATENT AND TRADEMARK OFFICE
CERTIFICATE OF CORRECTION

PATENT NO. : 5,939,409
DATED : August 17, 1999
INVENTOR(S) : Andersson, et al.

Page 2 of 2

It is certified that error appears in the above-identified patent and that said Letters Patent is hereby corrected as shown below:

and substitute therefor

--

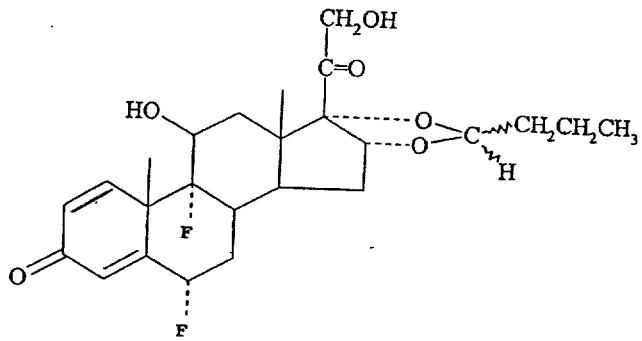

--

Signed and Sealed this

Twenty-sixth Day of September, 2000

Attest:

Q. TODD DICKINSON

Attesting Officer

Director of Patents and Trademarks